United States Patent [19]
Orenga

[11] Patent Number: 5,534,415
[45] Date of Patent: Jul. 9, 1996

[54] SELECTIVE AND DIFFERENTIAL MEDIUM FOR THE GROWTH AND DETECTION OF CANDIDA ALBICANS

[75] Inventor: Sylvain Orenga, Lyon, France

[73] Assignee: Bio Merieux, Marcy L'Etoile, France

[21] Appl. No.: 265,107

[22] Filed: Jun. 24, 1994

Related U.S. Application Data

[63] Continuation-in-part of Ser. No. 980,727, Nov. 24, 1992, abandoned.

[30] Foreign Application Priority Data

Nov. 25, 1991 [FR] France ..................................... 91 14972

[51] Int. Cl.$^6$ .............................. C12Q 1/04; C12Q 1/02; C12Q 1/34; C12Q 1/24
[52] U.S. Cl. .................. 435/34; 435/29; 435/22; 435/18; 435/4; 435/30; 435/14; 435/810; 435/975; 435/255.1; 435/255.4
[58] Field of Search .................. 435/34, 29, 22, 435/18, 4, 14, 30, 810, 975, 255.1, 255.4

[56] References Cited

U.S. PATENT DOCUMENTS

| | | | |
|---|---|---|---|
| 3,870,600 | 3/1975 | Youssef | 435/34 |
| 4,634,663 | 1/1987 | Horivchi | 435/25 |
| 4,874,695 | 10/1989 | Pincus | 435/34 |
| 5,081,033 | 1/1992 | Dorn et al. | 435/34 |

FOREIGN PATENT DOCUMENTS 56-030000  3/1981  Japan.

OTHER PUBLICATIONS

Difco Manual, "Dehydrated Culture Media & Reagents for Microb," 10th Edition, pp. 21, 1135–1136. (1984).
Mattia et al, J. of Bact, pp. 555–562, vol. 152, No. 2, 1982.
Nakao et al, Europ. Surg. Res, vol. 26, pp. 194–200, 1994.
Schoenborn, Christina, Jena Rev., vol. 16(4), p. 221 (Abstract) (1971).
Dalton et al., "Rapid Identification of Candida Albicans Using 4–methylumbelliferyl n–acetyl–beta–galactosaminide", Diagnostic Microbiology and Infectious Disease, vol. 12, No. 6, 1989, pp. 521–523.
Manafi et al., "Rapid Identification of Candida Albicans by Fluoroplate Candida Agar", Journal of Microbiological Methods, vol. 14, No. 2, Aug. 1991, pp. 103–108.
Perry et al., "Umbelliferyl–labeled Galactosaminide as an Aid in Identification of Candida Albicans", Journal of Clinical Microbiology, vol. 12, No. 6, Dec. 1987, pp. 2424–2425.
"DIFCO Manual", Jun. 11, 1987, pp. 21 and 1135–1136.

Primary Examiner—John Kight
Assistant Examiner—Louise N. Leary
Attorney, Agent, or Firm—Oliff & Berridge

[57] ABSTRACT

A method and culture and detection medium for selectively detecting yeasts of the species *Candida albicans* involving placing a sample to be analyzed directly in contact with (1) a culture and detection medium containing a nutrient base metabolized by yeasts, (2) a chromogenic or fluorigenic substrate capable of being hydrolyzed by a hexosaminidase enzyme that is associated with *Candida albicans*, and (3) at least one hexosaminidase-containing compound capable of activating hexosaminidase enzymes. A kit for carrying out the method for selectively detecting yeasts of the species *Candida albicans* is also provided.

49 Claims, No Drawings

SELECTIVE AND DIFFERENTIAL MEDIUM FOR THE GROWTH AND DETECTION OF CANDIDA ALBICANS

This is a continuation-in-part of application Ser. No. 07/980,727, filed Nov. 24, 1992, now abandoned.

The invention relates to the identification of yeasts of the species *Candida albicans*, by inoculation of a specific culture medium with a sample assumed to contain said yeasts, growth of the latter on the culture medium and development on said medium of a chromogenic or fluorigenic characterization phenomenon using a biochemical property specific to the yeast species.

BACKGROUND OF THE INVENTION

Indeed, a biochemical property exists which is specific to *Candida albicans* consisting in an enzymatic activity exerted by an enzyme belonging to the group comprising hexosaminidases and present in the species *Candida albicans*.

The determination of this enzymatic activity is the subject of a test using a culture and detection medium, marketed by Merck-Clevenot laboratories under the trademark Fluoroplate Candida Agar, comprising a nutrient base metabolized by yeasts, and a fluorigenic substrate capable of being hydrolyzed by N-acetyl-β-D-galactosaminidase releasing a fluorescent product. The fluorigenic substrate is 4-methylumbelliferyl-N-acetyl-β-D-galactosaminide, also termed 4-methylumbelliferyl-2-acetamido-2-deoxy-β-D-galactopyranoside. Enzymatic hydrolysis of the latter by *Candida albicans* releases 4-methylumbelliferone, a blue fluorescent product detectable under UV radiation at 360 nm.

This test has also been described in the following document: M Manafi et al, Journal of Microbiological Methods, vol 14, No 2, 1st Aug. 1991, Amsterdam, NL, pages 103–108.

Other documents have also described, with an appropriate nutrient base, the same fluorigenic substrate or a different chromogenic substrate, capable of being hydrolyzed by an enzyme of the hexosaminidase type to release a colored or fluorescent product:

J. L. Perry et al, Journal of Clinical Microbiology, vol 12, No. 6, 1989, Washington D.C., USA, pages 2424–2425 and MT Dalton et al, Diagnostic Microbiology and Infections [sic] Disease, vol 12, No. 6, 1989, New York, pages 521–523 have described more particularly the use of 4-methylumbelliferyl-N-acetyl-β-D-galactosaminide, also termed 4-methylumbelliferyl-2-acetamido-2-deoxy-β-D-galactopyranoside.

However, besides the fact that these detection media require the use of a source of UV radiation to visualize the reaction, the latter is only faintly detectable after 24 hours and is faintly detectable after 48 hours, making the test unusable within the context of rapid detection.

Furthermore, diffusion, in the medium, of the fluorescent product released by enzymatic hydrolysis reduces the probability of detecting *Candida albicans* in a plurimicrobial culture.

The problem of developing a method for selectively and rapidly detecting *Candida albicans* is therefore not yet resolved. Nevertheless, there is a great need given that *Candida albicans* is the species most commonly isolated from clinical samples and causes more or less severe infections of the skin, nails and mucous membranes in individuals with normal immune defenses, and very serious infections in weakened individuals and in particular those infected with the HIV virus.

SUMMARY OF THE INVENTION

According to the present invention, a method for the rapid and selective detection of *Candida albicans*, and a selective method for their culture and detection, have been developed making it possible to overcome the disadvantages of the abovementioned test.

The invention also provides a device for microbiological characterization comprising said medium for the culture and detection of *Candida albicans*, designed to allow both inoculation of a test sample into the medium and incubation of the test sample.

DETAILED DESCRIPTION OF PREFERRED EMBODIMENT

The method of according to the invention comprises:

a) providing a detection medium comprising a nutrient base metabolized by said yeasts, a fluorogenic or chromogenic substrate capable of being hydrolyzed by an enzyme characteristic of said yeasts selected from the group consisting of hexosaminidases, to release a marker and an hexosamine portion, and an activator selected from the group consisting of hexosamine-containing compounds which are different from said substrate, and which do not inhibit the hydrolysis of said substrate by said enzyme, b) providing a sample assumed to contain said yeasts, c) contacting said sample with said detection medium, d) incubating said sample contacted with said detection medium in step c), whereby in case of the presence of said yeasts, the fluorogenic or chromogenic substrate is split into said marker and said hexosamine portion, in addition to said activator, e) observing the absence or the presence of said marker in the mixture of step d).

The selective detection medium of this invention comprises a nutrient base metabolized by said yeasts, a fluorogenic or chromogenic substrate capable of being hydrolyzed by an enzyme characteristic of said yeasts, selected from the group consisting of hexosaminidases, to release a marker, said substrate comprising an hexosamine-portion and a fluorogenic or chromogenic radical attached thereto by an oxygen carried by anomeric carbon, and an activator selected from the group consisting of hexosamine-containing compounds which are different from said substrate.

According to a specific embodiment of the invention, the activator is a simple hexosamine which may be identical to or different from the hexosamine portion of the substrate.

The activator is a molecule and the hexosamine portion of the substrate is a radical, accordingly, it can be understood why they are identical except for a hydrogen atom.

In the case of simple hexosamines, the latter are selected from the group comprising of hexosamines and N-substituted hexosamines. Preferred hexosamines are glucosamine, galactosamine, and mannosamine and preferred N-substitued hexosamines are 2-acetamido-2-deoxyhexoses.

When said activator is identical to or different from the hexosamine portion of the substrate, it is observed that, contrary to the expected retroinhibitory effect, the compound behaves in the medium of the invention inoculated with *Candida albicans* as an excellent activator of hexosaminidases.

According to another specific embodiment of the invention, the activator belongs to the group comprising complex hexosamines, and constitutes a structural analog of the substrate, comprising a hexosamine moiety and an aglycon. Said aglycon is preferably selected from the group consisting of substituted or unsubstituted, linear or branched alkyl groups having 1 to 20 carbon atoms, preferably 1 to 10 carbon atoms, and especially a methyl or isopropyl group, and substituted or unsubstituted, linear or branched alkylene groups having 1 to 20 carbon atoms, preferably 1 to 10 carbon atoms, and substituted or unsubstituted aromatic or heterocyclic group having 6 to 10 carbon atoms, and especially a phenyl group. In the case where said alkyl or alkylene group is substituted, it is preferably by a thiol group.

When the activator is a structural analog of the substrate, said compound may be selected especially from:

the structural analogs of the substrate whose hexosamine portion is identical to that of the substrate and the aglycon attached to the oxygen carried by the anomeric carbon is different from the chromogenic or fluorigenic radical of the substrate, and the structural analogs of the substrate whose hexosamine portion is different from that of the substrate and the aglycon attached to the oxygen carried by anomeric carbon is identical to the chromogenic or fluorigenic radical of the substrate.

The activating role of the activator, when it is a structural analog of the substrate, it also surprising insofar as it would be logical to expect in this case a phenomenon of inhibition of competition between the activator and the fluorigenic or chromogenic substrate.

By virtue of the invention, and as demonstrated by the experimental procedure laid out below, the enzymatic hydrolysis reaction can be easily detected after 24 hours of incubation.

The composition of the culture medium, expressed in g/l of final medium, is set out below in a general manner.

The medium comprises a nutrient base essential for the development of the yeasts, and activators of the hexosaminidase according to the present invention.

The constituent elements of the nutrient base comprise:

peptones, from 0.01 to 40 g/l, such as meat peptone, the product marketed by the Company Biomerieux under the trademark bioSoyase or analog, or alternatively a mixture of peptones; preferably, the peptone or mixture of peptones is present in the medium at about 6 g/l±0.5 g/l;

a yeast extract, from 0.01 to 40 g/l, preferably about 1.5 g/l, providing vitamins for growth of the yeasts;

a carbon source, such as glucose, glycerol, an acetate, a pyruvate, a lactate, arginine, an aminobutyrate, or a mixture of these components, in a proportion of 0 to 10 g/l; the carbon source is preferably glucose in an amount of 1 g/l;

a buffer added to the medium in order to obtain a pH of between 5 and 8.5 which is appropriate for the development of *Candida albicans*; the buffer is chosen from phosphate, Tris, Hepes (N-2-hydroxyethylpiperazine-N'-2-ethasulfonic acid) and citrate buffers in a proportion of 2.5 to 100 mM; preferably, the buffer is a 10 mM phosphate buffer for adjusting the pH of the medium to a value in the region of 7;

Agar, from 11 to 20 g/l, preferably 15 g/l.

The chromogenic or fluorigenic substrate may be any chromogenic or fluorigenic substrate which can be hydrolyzed by a hexosaminidase, such as a galactosaminidase, glucosamidase or mannosaminidase, to release a colored or fluorescent product. Preferably, the substrate is chosen from those which are highly colored or fluorescent with few molecules, which do not induce modifications of the metabolism of the microorganisms, except for the desired enzymatic activity, which do not require, for the detection of the colored or fluorescent product, termed marker, a reagent which is toxic to the microorganisms, which possess good water-solubility, which release after hydrolysis a marker that does not diffuse or that hardly diffuses in the medium, in order that the signal remains limited to the immediate vicinity of the colonies, and which produce a signal which is visualized without necessarily requiring the use of an apparatus such as a UV lamp or a spectrophotometer. These substrates are preferably chosen, for the chromogenic substrates, from those comprising a chromophoric group such as a substituted or unsubstituted indolyl, and especially from 5-bromo-4-chloro-3-indolyl-N-acetyl-β-D-glucosamine, also termed 5-bromo-4-chloro-3-indolyl-2-acetamido-2-deoxy-β-D-glucopyranoside; 5-bromo-4-chloro-3-indolyl-N-acetyl-β-D-galactosamine, also termed 5-bromo-4-chloro-3-indolyl-2-acetamido-2-deoxy-β-D-galactopyranoside; from 20 to 600 μM, advantageously 5-bromo-4-chloro-3-indolyl-2-acetamido-2-deoxy-β-D-glucopyranoside at 200 μM and, for the fluorigenic substrates, from 4-methylumbelliferyl-2-acetamido-2-deoxy-β-D-galactopyranoside, and 4-methylumbelliferyl-2-acetamido-2-deoxy-β-D-glucopyranoside.

The amount of the hexosamine-containing compound is between 0.01 and 20 g/l, preferably between 0.1 and 5 g/l. Preferably, the activator chosen is 2-acetamido-2-deoxyglucose in an amount of 1 g/l.

Other activators may be added to the medium to promote the activity of the hexosaminidase. These activators are chosen from the group comprising divalent cationic compounds such as $Mn^{2+}$, $Mg^{2+}$ or $Ca^{2+}$ salts or a mixture of the latter, from 0 to 10 mM. Preferably, the divalent cationic compound chosen is an $Mn^{2+}$ salt (1 mM).

Permeability-enhancing and/or surface-active agents which may be added to the medium to promote good enzyme-substrate contact are chosen from the group consisting of the bile salts, sodium deoxycholate, the polyoxyethylene glycol and alkylphenol ethers, marketed for example under the trademark Triton®, the sorbitan and fatty acid esters, marketed for example under the trademark Tween®, at a concentration of 0 to 5 g/l. Preferably, the permeability-enhancing agent is sodium deoxycholate in an amount of 0.1 g/l.

A bacteria inhibitor or a mixture of bacteria inhibitors which makes it possible to inhibit the growth of Gram+ and Gram– bacteria, without affecting that of yeasts and if possible fungi, may be added to the medium. Preferably, the bacteria inhibitors are chosen from the group comprising antibiotics such as gentamicin, chloramphenicol, penicillin, streptomycin, cycloheximide, neomycin, tetracycline, oxytetracycline or a mixture of antibiotics, and/or from tellurite, a molybdate and analogs, or their mixtures. Advantageously, chloramphenicol (0.5 g/l) or a mixture of gentamicin (0.1 g/l) and chloramphenicol (0.05 g/l) is chosen. It is also possible to inhibit the growth of bacteria by reducing the pH of the medium to an acidic pH.

The characteristics and advantages of the invention are now set out supported by Examples 1 to 7.

EXAMPLE 1

A composition of the preferred medium is given below for 1 liter:

| | |
|---|---|
| bioSoyase (BIOMERIEUX) | 6.0 g |
| yeast extract (BIOMERIEUX) | 1.5 g |
| glucose (MERCK) | 1.0 g |
| 2-acetamido-2-deoxyglucose.(SIGMA) | 1.0 g |
| phosphate buffer (MERCK) | 10.0 mmol |
| $Mn^{2+}$ (MERCK) | 1.0 mmol |
| sodium deoxycholate (MERCK) | 0.1 g |
| or 5-bromo-4-chloro-3-indolyl-2-acetamido-2-deoxy-β-D-glucopyranoside (BIOSYNTH). | 0.1 g |
| agar (BIOMERIEUX) | 15.0 g |
| gentamicin | 0.1 g |
| chloramphenicol | 0.05 g |
| pH | 7.0 |

EXAMPLE 2

Assays were carried out in order to test the media of the invention and to compare them with conventional media.

Two media were prepared according to the usual techniques. The first medium, designated below Medium I, contains all the elements of the nutrient base as well as a chromogenic substrate of a hexosaminidase and a bacteria inhibitor.

The composition of Medium I for one liter of final medium is the following:

| | |
|---|---|
| bioSoyase (BIOMERIEUX) | 6.0 g |
| yeast extract (BIOMERIEUX) | 1.5 g |
| glucose (MERCK) | 1.0 g |
| phosphate buffer (MERCK) | 10.0 mmol |
| or 5-bromo-4-chloro-3-indolyl-2-acetamido-2-deoxy-β-D-glucopyranoside (BIOSYNTH) | 0.1 g |
| agar (BIOMERIEUX) | 15.0 g |
| gentamicin | 0.1 g |
| chloramphenicol | 0.05 g |

The pH of the medium was adjusted to about 7.

The second medium, called Medium II, corresponds to the medium according to the invention and contains all the elements described above for Medium I, plus the activators of the present invention, that is to say a hexosamine-containing compound, a permeability-enhancing agent and divalent cations. The composition of the Medium II corresponds to that described in Example 1.

15 yeast strains were directly cultured on these two media in Petri dishes. The strains, derived from the Applicant's collection, belong to the following species: *Candida albicans*: eight strains, *Candida glabrata*: three strains, *Candida tropicalis*: four strains. The dishes were incubated at 37° C. for 48 hours. The colonies formed were visually examined, after 24 and 48 hours of incubation respectively, based on the following interpretations:

the blue colonies correspond to *Candida albicans* strains producing N-acetyl-β-D-glucosaminidase;

the white colonies correspond to the strains which do not produce the abovementioned enzyme and which therefore belong to other yeast species which will therefore be identified by means of the usual techniques.

The results are presented in Table I below:

TABLE I

| | | Coloration after 24 hours | | | after 48 hours | | |
|---|---|---|---|---|---|---|---|
| Species | Medium | Strong | Weak | None | Strong | Weak | None |
| C. albicans | Medium I | 0* | 3 | 5 | 3 | 4 | 1 |
| | Medium II | 6 | 2 | 0 | 7 | 1 | 0 |
| C. glabrata | Medium I | 0 | 0 | 3 | 0 | 0 | 3 |
| | Medium II | 0 | 0 | 3 | 0 | 0 | 3 |
| C. tropicalis | Medium I | 0 | 0 | 4 | 0 | 1 | 3 |
| | Medium II | 0 | 0 | 4 | 0 | 1 | 3 |

*number of strains

As evident from the above table, the introduction of the hexosaminidase activator allows a much earlier detection of the *Candida albicans* strains. Indeed, all the strains are colored from 24 hours onwards on the medium according to the invention, six out of eight being highly colored whereas only three are very faintly colored on the conventional medium.

EXAMPLE 3

The assays carried out in Example 2 were repeated in this example with the same conventional medium I and a medium III according to the invention in which the activator of medium II, that is to say 2-acetamido-2-deoxyglucose, was replaced by an activator which is a structural analog of the substrate, namely methyl-2-acetamido-2-deoxy-β-D-glucopyranoside.

The concentration of the activator in medium III is 50 mg/l.

The other constituents of medium III remain the same as those of medium II.

The results of the assays are presented in Table II below:

TABLE II

| Species | Medium | Coloration after 24 hours | | | after 48 hours | | |
|---|---|---|---|---|---|---|---|
| | | Strong | Weak | None | Strong | Weak | None |
| C. albicans | Medium I | 0* | 3 | 5 | 3 | 4 | 1 |
| | Medium III | 5 | 3 | 0 | 7 | 1 | 0 |
| C. glabrata | Medium I | 0 | 0 | 3 | 0 | 0 | 3 |
| | Medium III | 0 | 0 | 3 | 0 | 0 | 3 |
| C. tropicalis | Medium I | 0 | 0 | 4 | 0 | 1 | 3 |
| | Medium III | 0 | 0 | 4 | 0 | 1 | 3 |

*number of strains

As in the previous example, the introduction of the hexosaminidase activator allows a much earlier detection of the *Candida albicans* strains. Indeed, all the strains are colored from 24 hours onwards on the medium according to the invention, five out of eight being highly colored whereas only three are very faintly colored on the conventional medium.

EXAMPLE 4

42 yeast or bacterial strains were placed on medium II of the present invention. All of these strains are derived from the Applicant's collection and are divided up as follows:

8 *Candida albicans*
3 *Candida* (Torulopsis) *glabrata*
2 *Candida guilliermondii*
2 *Candida kursei*
2 *Candida lusitaniae*
3 *Candida parapsilosis*
3 *Candida pseudotropicalis*
2 *Candida rugosa*
2 *Candida stellatoidea*
4 *Candida tropicalis*
3 *Cryptococcus neoformans*
2 *Saccharomyces cerevisiae*
2 *Trichosporon cutaneum*
2 *Serraria marcescens*
2 *Staphylococcus aureus*

The Petri dishes containing the medium of the present invention were inoculated, according to the usual procedure, with each of the strains described above. The dishes were incubated at 37° C. for 48 hours. The colonies formed were visually examined after 24 and 48 hours of incubation respectively.

Of the 42 isolates, only the eight *Candida albicans* strains gave blue colonies after 24 hours of incubation, which coloration characterizes *Candida albicans* on the medium of the invention, six of these strains being very highly colored and two slightly less highly colored. After 48 hours of incubation, 7 of the 8 *Candida albicans* strains give colonies which are highly colored in blue, only one being only faintly colored.

Of the other yeast species, only the *Trichosporon cutaneum* strains show no growth after 24 hours, and practically none after 48 hours. All the other yeast strains give small white colonies after 24 hours, which increase in size after 48 hours. For one *Candida tropicalis* strain and the two *Candida stelloroidea* strains, white colonies are observed after 24 hours of incubation which become very faintly colored in blue after 48 hours of incubation.

Depending on the intensity of the signal obtained with the medium of the present invention for the detection of *Candida albicans*, it is impossible to confuse the very weak coloration obtained with these other two species after 48 hours of incubation, for that obtained for *Candida albicans*, even in the case of more faintly colored *Candida albicans* strains.

Moreover, in the case of the bacterial strains, that is to say *Serraria marcescens* and *Staphylococcus aureus*, none of these strains produces colonies, even after 48 hours of incubation.

It is therefore evident from these assays that the medium of the invention exhibits a very high sensitivity and specificity for *Candida albicans*, and makes it possible to detect and identify, directly and without ambiguity, the *Candida albicans* strains which alone produce blue colonies after 24 hours of incubation.

EXAMPLE 5

A comparison was made between the medium marketed by MERCK under the name Fluoroplate Candida Agar and the medium according to the invention.

The 42 strains of the previous example were cultured in Petri dishes on each of these media respectively. The dishes were incubated at 37° C. for 48 hours and the colonies formed were visually examined after 24 and 48 hours of incubation.

On the medium of the invention, the colonies expressing a hexosaminidase activity are blue whereas, on the MERCK medium, they exhibit a blue fluorescence after observation under a UV lamp at 360 nm.

The results are presented in Table III below.

TABLE III

| Species (No. of strains) | Medium | Coloration (medium according to the invention) Fluorescence (Merck medium) | | | | | |
|---|---|---|---|---|---|---|---|
| | | after 24 hours | | | after 48 hours | | |
| | | Strong | Weak | None | Strong | Weak | None |
| C. albicans (8) | Medium according to the invention | 6* | 2 | 0 | 7 | 1 | 0 |
| | Fluoroplate Candida agar | 0 | 3 | 5 | 4 | 3 | 1 |
| C. glabrata (3) | Medium according to the invention | 0 | 0 | 3 | 0 | 0 | 3 |
| | Fluoroplate Candida agar | 0 | 0 | 3 | 0 | 0 | 3 |
| C. guillermondii (2) | Medium according to the invention | 0 | 0 | 2 | 0 | 0 | 2 |
| | Fluoroplate Candida agar | 0 | 0 | 2 | 0 | 0 | 2 |
| C. krusei (2) | Medium according to the invention | 0 | 0 | 2 | 0 | 0 | 2 |
| | Fluoroplate Candida agar | 0 | 0 | 2 | 0 | 0 | 2 |
| C. lusitaniae (2) | Medium according to the invention | 0 | 0 | 2 | 0 | 0 | 2 |
| | Fluoroplate Candida agar | 0 | 0 | 2 | 0 | 0 | 2 |
| C. parapsilosis (3) | Medium according to the invention | 0 | 0 | 3 | 0 | 0 | 3 |
| | Fluoroplate Candida agar | 0 | 0 | 3 | 0 | 0 | 3 |
| C. pseudotropicalis (3) | Medium according to the invention | 0 | 0 | 3 | 0 | 0 | 3 |
| | Fluoroplate Candida agar | 0 | 0 | 3 | 0 | 0 | 3 |
| C. rugosa (2) | Medium according to the invention | 0 | 0 | 2 | 0 | 0 | 2 |
| | Fluoroplate Candida agar | 0 | 1 | 1 | 1 | 1 | 0 |
| C. stellatoidea (2) | Medium according to the invention | 0 | 0 | 2 | 0 | 2 | 0 |
| | Fluoroplate Candida agar | 0 | 1 | 1 | 0 | 2 | 0 |
| C. tropicalis (4) | Medium according to the invention | 0 | 0 | 4 | 0 | 1 | 3 |
| | Fluoroplate Candida agar | 0 | 0 | 4 | 0 | 1 | 3 |
| Cryptococcus neoformans (3) | Medium according to the invention | 0 | 0 | 3 | 0 | 0 | 3 |
| | Fluoroplate Candida agar | 0 | 0 | 3 | 0 | 0 | 3 |
| S. cerevisiae (2) | Medium according to the invention | 0 | 0 | 2 | 0 | 0 | 2 |
| | Fluoroplate Candida agar | 0 | 0 | 2 | 0 | 0 | 2 |
| T. cutaneum (2) | Medium according to the invention | 0 | 0 | 2 | 0 | 0 | 2 |
| | Fluoroplate Candida agar | 0 | 2 | 0 | 2 | 0 | 0 |
| S. marcescens (2) | Medium according to the invention | 0 | 0 | 2 | 0 | 0 | 2 |
| | Fluoroplate Candida agar | 0 | 1 | 1 | 2 | 0 | 0 |
| Staph. aureus (2) | Medium according to the invention | 0 | 0 | 2 | 0 | 0 | 2 |
| | Fluoroplate Candida agar | 0 | 0 | 2 | 0 | 0 | 2 |

*number of strains

As evident from the above table, the 8 candida albicans strains are detected from 24 hours onwards, in most cases with a very strong coloration with the medium of the invention, whereas only three strains produce a weak fluorescence after 24 hours of incubation on the medium marketed by the company MERCK. Likewise, after 48 hours of incubation, it is observed that 7 Candida albicans strains are detected with a very strong coloration, against only 4 with the Fluoroplate Candida Agar medium. These results demonstrate the excellent sensitivity of the medium of the present invention compared with that of the previous medium.

Moreover, the medium of the present invention possesses a very high specificity since no false positives are observed after 24 hours whereas 4 strains other than Candida albicans exhibit a fluorescence with the Fluoroplate Candida Agar medium. After 48 hours of incubation, 3 strains not belonging to the *Candida albicans* species appear very faintly colored with the medium of the invention, against 9 with the other medium, some of which are very highly colored.

Finally, an excellent selectivity is observed for the medium according to the invention with respect to bacteria, which prevents masking of the presence of yeasts in samples highly contaminated with bacteria, which may also possess a hexosaminidase.

In addition to the excellent sensitivity, specificity and selectivity obtained with the medium of the present invention, the latter also has the advantage of allowing a coloration to be read from 24 hours onwards, which is possible directly on the medium with the naked eye. Furthermore, the intense coloration obtained with the medium of the present invention, limited to the colony, allows detection of plurimicrobial cultures, whereas the fluorescence on the commercial medium diffuses throughout the agar.

EXAMPLE 6

The assays carried out in Example 2 with medium II were repeated in this example except that different concentrations of 2-acetamido-2-deoxyglucose ranging from 0 to 20,0 g/l were tested.

As evident from the above table, when the concentration of the activator is lower than 0,1 g/l, no activation effect is observed. An activation is proved for concentration ranging from 0,1 g/l to 5 g/l. At a higher concentration said activator behaves as a feedback inhibitor.

In said medium II, after the substrate is totally hydrolyzed, about 0,025 g/l of 2-acetamido-2-deoxyglucose is released. At such a concentration, the activator has not yet an activation effect. This shows that the substrate itself, even after hydrolysis cannot act as an activator.

EXAMPLE 7

The same assays carried out in Example 6 (with medium II) were repeated in this example except that the activator 2-acetamido-2-deoxyglucose was replaced by phenyl-2-acetamido-2-deoxyglucose for different concentrations ranging from 0 to 1 g/l.

TABLE IV

| | | COLORATION | | | | | |
|---|---|---|---|---|---|---|---|
| | 2-acetamido-2 | After 24 hours | | | After 48 hours | | |
| Species | deoxyglucose (g/l) | Strong | Weak | None | Strong | Weak | None |
| C. albicans | 0,000 | 0* | 3 | 5 | 3 | 4 | 1 |
| | 0,005 | 0 | 3 | 5 | 3 | 4 | 1 |
| | 0,010 | 0 | 3 | 5 | 4 | 3 | 1 |
| | 0,025 | 0 | 3 | 5 | 4 | 3 | 1 |
| | 0,050 | 0 | 5 | 3 | 5 | 2 | 1 |
| | 0,10 | 2 | 4 | 2 | 5 | 3 | 0 |
| | 0,25 | 3 | 4 | 1 | 6 | 2 | 0 |
| | 0,50 | 4 | 3 | 1 | 6 | 2 | 0 |
| | 1,0 | 6 | 2 | 0 | 7 | 1 | 0 |
| | 2,5 | 6 | 2 | 0 | 7 | 1 | 0 |
| | 5,0 | 3 | 5 | 0 | 4 | 4 | 0 |
| | 10,0 | 1 | 4 | 3 | 2 | 5 | 1 |
| | 20,0 | 0 | 4 | 4 | 1 | 6 | 1 |
| C. glabrata | 0,000 | 0 | 0 | 3 | 0 | 0 | 3 |
| | 0,005 | 0 | 0 | 3 | 0 | 0 | 3 |
| | 0,010 | 0 | 0 | 3 | 0 | 0 | 3 |
| | 0,025 | 0 | 0 | 3 | 0 | 0 | 3 |
| | 0,050 | 0 | 0 | 3 | 0 | 0 | 3 |
| | 0,10 | 0 | 0 | 3 | 0 | 0 | 3 |
| | 0,25 | 0 | 0 | 3 | 0 | 0 | 3 |
| | 0,50 | 0 | 0 | 3 | 0 | 0 | 3 |
| | 1,0 | 0 | 0 | 3 | 0 | 0 | 3 |
| | 2,5 | 0 | 0 | 3 | 0 | 0 | 3 |
| | 5,0 | 0 | 0 | 3 | 0 | 0 | 3 |
| | 10,0 | 0 | 0 | 3 | 0 | 0 | 3 |
| | 20,0 | 0 | 0 | 3 | 0 | 0 | 3 |
| C. tropicalis | 0,000 | 0 | 0 | 4 | 0 | 1 | 3 |
| | 0,005 | 0 | 0 | 4 | 0 | 1 | 3 |
| | 0,010 | 0 | 0 | 4 | 0 | 1 | 3 |
| | 0,025 | 0 | 0 | 4 | 0 | 1 | 3 |
| | 0,050 | 0 | 0 | 4 | 0 | 1 | 3 |
| | 0,10 | 0 | 0 | 4 | 0 | 1 | 3 |
| | 0,25 | 0 | 0 | 4 | 0 | 2 | 2 |
| | 0,50 | 0 | 0 | 4 | 0 | 1 | 3 |
| | 1,0 | 0 | 0 | 4 | 0 | 1 | 3 |
| | 2,5 | 0 | 0 | 4 | 0 | 1 | 3 |
| | 5,0 | 0 | 0 | 4 | 0 | 1 | 3 |
| | 10,0 | 0 | 0 | 4 | 0 | 1 | 3 |
| | 20,0 | 0 | 0 | 4 | 0 | 1 | 3 |

*number of strains

TABLE V

| Species | Phenyl-2-acetamido-2 deoxyglucose g/l | Coloration After 24 hours | | | After 48 hours | | |
|---|---|---|---|---|---|---|---|
| | | Strong | Week | None | Strong | Weak | None |
| C. albicans | 0,000 | 0* | 3 | 5 | 3 | 4 | 1 |
| | 0,001 | 0 | 3 | 5 | 3 | 4 | 1 |
| | 0,005 | 0 | 3 | 5 | 3 | 4 | 1 |
| | 0,010 | 0 | 3 | 5 | 3 | 4 | 1 |
| | 0,025 | 0 | 3 | 5 | 4 | 3 | 1 |
| | 0,050 | 0 | 4 | 4 | 4 | 3 | 1 |
| | 0,10 | 0 | 4 | 4 | 4 | 3 | 1 |
| | 0,25 | 1 | 3 | 4 | 5 | 2 | 1 |
| | 0,50 | 2 | 3 | 3 | 5 | 3 | 0 |
| | 1,0 | 2 | 3 | 3 | 5 | 3 | 0 |
| C. glabrata | 0,000 | 0 | 0 | 3 | 0 | 0 | 3 |
| | 0,001 | 0 | 0 | 3 | 0 | 0 | 3 |
| | 0,005 | 0 | 0 | 3 | 0 | 0 | 3 |
| | 0,010 | 0 | 0 | 3 | 0 | 0 | 3 |
| | 0,025 | 0 | 0 | 3 | 0 | 0 | 3 |
| | 0,050 | 0 | 0 | 3 | 0 | 0 | 3 |
| | 0,10 | 0 | 0 | 3 | 0 | 0 | 3 |
| | 0,25 | 0 | 0 | 3 | 0 | 0 | 3 |
| | 0,50 | 0 | 0 | 3 | 0 | 0 | 3 |
| | 1,0 | 0 | 0 | 3 | 0 | 0 | 3 |
| C. tropicalis | 0,000 | 0 | 0 | 4 | 0 | 1 | 3 |
| | 0,001 | 0 | 0 | 4 | 0 | 1 | 3 |
| | 0,005 | 0 | 0 | 4 | 0 | 1 | 3 |
| | 0,010 | 0 | 0 | 4 | 0 | 1 | 3 |
| | 0,025 | 0 | 0 | 4 | 0 | 1 | 3 |
| | 0,050 | 0 | 0 | 4 | 0 | 1 | 3 |
| | 0,10 | 0 | 0 | 4 | 0 | 1 | 3 |
| | 0,25 | 0 | 0 | 4 | 0 | 1 | 3 |
| | 0,50 | 0 | 0 | 4 | 0 | 1 | 3 |
| | 1,0 | 0 | 0 | 4 | 0 | 1 | 3 |

*number of strains

In this case, the activator phenyl-2-acetamido-2-deoxyglucose, is a structural analog of the substrate, comprising an hexosamine moiety identical to the hexosamine portion of said substrate. As evident from table V, no inhibitor effect is observed but an activation is observed from a concentration for 0,25 g/l. The higher observation is showed for a concentration of 1 g/l.

EXAMPLE 8

An assay was carried out to determine the minimum number of *Candida albicans* colonies which can be detected, from a mixture of microorganisms, on the medium of the invention.

This assay was carried out on the following 4 strains:

*Candida albicans*, BIOMERIEUX reference 19

*Candida (Torulopsis)glabrata*, BIOMERIEUX reference 154

*Candida tropicalis*, BIOMERIEUX reference 47

*Serratia marcescens*, BIOMERIEUX reference 106.

These strains were cultured for 24 hours at 37° C. on agar marketed under the name Sabouraud. A suspension in physiological saline was prepared for each strain, adjusted by means of a nephelometer so as to obtain about $10^8$ germs/ml. These suspensions were then diluted $10^4$-fold. For the *Candida albicans* strain, the latter suspension was diluted 10-and 50-fold, thus making it possible to have available three dilutions of the initial suspension: $10^4$, $10^5$ and $5.10^5$. The different suspensions of the *Candida albicans* strain were then mixed in equal volumes with those for the other three strains.

20 μl of each of these mixtures were deposited on Petri dishes containing the medium of the invention and plated by means of a bent sterile Pasteur pipette. After absorption, the dish is inverted and incubated for 24 hours at 37° C. The white and blue colonies are counted for each dish. The results are presented in Table V below.

TABLE VI

| Dilutions in the mixture C. albicans/ Other strain | Species in the mixture | | |
|---|---|---|---|
| | C. albicans + C. glabrata | C. albicans + C. tropicalis | C. albicans + S. marcesans |
| $10^4/10^4$ | 123/152* | 93/107 | 113/0 |
| $10^5/10^4$ | 9/119 | 12/122 | 11/0 |
| $5.10^5/10^4$ | 3/135 | 1/97 | 2/0 |

*number of blue colonies/number of white colonies.

From the results, it is apparent that on the medium of the invention, it is possible to detect, without any difficulty, the mixtures of *Candida albicans* strains, that is to say the blue colonies, with those of other yeast species, that is to say the white colonies. This detection is equally easy whether there is one colony per 100 or whether they are present in large numbers, the coloration of the *Candida albicans* colonies being invariable regardless of their number on the isolation medium. Furthermore, the presence of bacteria in the suspension does not in any way interfere with the development and the coloration of the *Candida albicans* strains on the medium of the invention.

EXAMPLE 9

Isolation of yeasts on the medium of the invention and use of kits for the identification and determination of resistances to antifungal agents.

Four yeast strains, derived from the Applicant's collection, were isolated on the medium of the invention, as well as on the Sabouraud Gentamicin Chloramphenicol medium (marketed by the company BIOMERIEUX). These strains belong to the following species:

2 Candida albicans

1 Candida tropicalis

1 Candida(Torulopsis)glabrata

For each isolate, after 24 hours of incubation at 37° C., colonies were used to inoculate, according to the instructions of the manufacturer, a yeast identification gallery ID 32 C (tradename, company BIOMERIEUX), and a gallery ATB Fungus (antifungigram) from the company BIOMERIEUX (registered trademark ATB). The colonies of *Candida albicans* strains on the medium of the invention exhibit a blue coloration.

The galleries are read after 24, 48 and 72 hours respectively and the results are noted on record cards. The results obtained for each strain isolated on the medium of the invention are identical to those obtained after isolation on the Sabouraud medium.

The yeast colonies, belonging or not belonging to the species *Candida albicans*, isolated on the medium of the invention, can be used for studying their resistance to antifungal agents or for inoculating yeast identification kits.

I claim:

1. A method for the rapid and selective detection of yeasts of the species *Candida albicans* comprising:
   a) providing a detection medium comprising a nutrient base metabolized by said yeasts, a fluorigenic or chromogenic substrate capable of being hydrolyzed by a hexosaminidase enzyme characteristic of said yeasts, to release a marker and a hexosamine portion, and an activator selected from the group consisting of hexosamine-containing compounds which are different from said substrate, and which do not inhibit the hydrolysis of said substrate by said enzyme,
   b) providing a sample assumed to contain said yeasts,
   c) contacting said sample with said detection medium,
   d) incubating said sample contacted with said detection medium in step c), whereby in case of the presence of said yeasts, the fluorigenic or chromogenic substrate is split into said marker and said hexosamine portion, in addition to said activator,
   e) visually observing the absence or the presence of said marker in the mixture of step d).

2. The method of claim 1, wherein said activator is a simple hexosamine selected from the group consisting of hexosamines and N-substituted hexosamines.

3. The method of claim 2, wherein said hexosamines are selected from the group consisting of glucosamine, galactosamine and mannosamine.

4. The method of claim 2, wherein said N-substituted hexosamines are selected from 2-acetamido-2-deoxyhexoses.

5. The method of claim 1, wherein said activator is a complex hexosamines selected from the group consisting of structural analogs of said substrate comprising an hexosamine moiety and an aglycon.

6. The method of claim 5, wherein said aglycon is selected from the group consisting of alkyl groups having 1 to 20 carbon atoms, alkylene groups having 1 to 20 carbon atoms, aromatic and heterocyclic groups having 6 to 10 carbon atoms.

7. The method of claim 6, wherein said alkyl group is selected from the group consisting of methyl and isopropyl groups.

8. The method of claim 6, wherein said aromatic group is a phenyl group.

9. The method of claim 5, wherein said hexosamine moiety is selected from the group consisting of simple hexosamines and N-acetyl-hexosamines.

10. The method of claim 1, wherein the fluorigenic substrate is selected from the group consisting of 4-methylumbelliferyl-2-acetamido-2-deoxy-β-D-galactopyranoside and 4-methylumbelliferyl-2-acetamido-2-deoxy-β-D-glucopyranoside.

11. The method of claim 1, wherein the chromogenic substrate is selected from the group 5-bromo-4-chloro-3-indolyl-2-acetamido-2-deoxy-β-D-glucopyranoside and 5-bromo-4-chloro-3-indolyl-2-acetamido-2-deoxy-β-D-galactopyranoside.

12. The method of claim 1, wherein the sample is incubated at about 37° C.

13. The method of claim 1, wherein the sample is contacted with the detection medium for about 24 hours.

14. The method of claim 1, wherein the sample is contacted with the detection medium for about 48 hours.

15. The method of claim 1, wherein the sample is incubated with the detection medium for about 24 hours.

16. The method of claim 1, wherein the sample is incubated with the detection medium for about 48 hours.

17. The method of claim 1, wherein the observation of the absence or presence of the marker is accomplished after about 24 hours.

18. The method of claim 1, wherein the observation of the absence or presence of the marker is accomplished after about 48 hours.

19. A selective detection medium for the culture and the detection of yeasts of the species *Candida albicans*, comprising a nutrient base metabolized by said yeasts, a fluorigenic or chromogenic substrate capable of being hydrolyzed by an enzyme characteristic of said yeasts selected from the group consisting of hexosaminidases, to release a marker, said substrate comprising an hexosamine-portion and a fluorigenic or chromogenic radical attached thereto by an oxygen carried by anomeric carbon, and an activator selected from the group consisting of hexosamine-containing compounds which are different from said substrate, and which do not inhibit the hydrolysis of said substrate by said enzyme.

20. The medium of claim 19, wherein said activator is a simple hexosamine selected from the group consisting of hexosamines and N-substituted hexosamines.

21. The medium of claim 20, wherein said hexosamines are selected from the group consisting of glucosamine, galactosamine and mannosamine.

22. The medium of claim 20, wherein said N-substituted hexosamine is a 2-acetamido-2-deoxyglucose.

23. The medium of claim 19, wherein said activator is a complex hexosamine selected from the group consisting of structural analogs of said substrate comprising an hexosamine moiety and an aglycon.

24. The medium of claim 23, wherein said aglycon is selected from the group consisting of alkyl groups having 1 to 20 carbon atoms, alkylene groups having 1 to 20 carbon atoms, aromatic and heterocyclic groups having 6 to 10 carbon atoms.

25. The medium of claim 24, wherein said alkyl group is selected from the group consisting of methyl and isopropyl groups.

26. The medium of claim 24, wherein said aromatic group is a phenyl group.

27. The medium of claim 23, wherein said hexosamine moiety is selected from the group consisting of simple hexosamines and N-acetyl-hexosamines.

28. The medium of claim 23, wherein the hexosamine moiety of said activator is identical to the hexosamine portion of the substrate, and the aglycon of said activator is different from the chromogenic or fluorogenic radical of said substrate.

29. The medium of claim 23, wherein the hexosamine moiety of said activator is different from the hexosamine portion of the substrate, and the aglycon of said activator is identical to the chromogenic or fluorogenic radical of said substrate.

30. The medium of claim 19, wherein the activator is present in a concentration ranging from 0,01 to 20 g par liter of medium.

31. The medium of claim 19, wherein the activator is present in a concentration ranging from 0,1 to 5 g per one liter of medium.

32. The medium of claim 22, wherein the activator is 2-acetamido-2-deoxyglucose in a concentration of 1 g per one liter of medium.

33. The medium of claim 19, further comprising at least one hexosaminidase activator selected from divalent cationic compounds.

34. The medium of claim 33, wherein the divalent cationic compounds are selected from $Mn^{2+}$ or $Ca^{2+}$ salts, and the molar concentration of said compounds in the medium is between 0 and 10 mM.

35. The medium of claim 34, wherein said divalent cationic compounds is an $Mn^{2+}$ salt, and its molar concentration in the medium is 1 mM.

36. The medium of claim 19, further comprising at least one agent which enhances the permeability of the yeast cell wall.

37. The medium of claim 19, further comprising at least one surface-active agent.

38. The medium of claim 36, wherein the agents are chosen from the group consisting of bile salts, sodium deoxycholate, polyoxyethylene glycol and alkylphenol ethers, and sorbitan and fatty acid esters.

39. The medium of claim 38, wherein said agents are present in the medium in an amount of between 0 and 5 g per liter of medium.

40. The medium of claim 19, further comprising a bacteria growth inhibitor.

41. The medium of claim 40, wherein said bacteria growth inhibitor consists of at least one antibiotic selected from gentamicin, chloramphenicol, penicillin, streptomycin, cycloheximide, neomycin, tetracycline and oxytetracycline.

42. The medium of claim 41, wherein said bacteria growth inhibitor is chloramphenicol in an amount of 0.5 g per liter of medium, or a mixture of gentamicin and chloramphenicol, in an amount of 0.1 g and 0.05 g per liter of medium respectively.

43. The medium of claim 40, wherein said bacteria growth inhibitor is selected from tellurite and molybdates.

44. The medium of claim 19, wherein the substrate is selected from the group consisting of 4-methylumbelliferyl-2-acetamido-2-deoxy-β-D-galacto-pyranoside, 4-methylumbelliferyl-2-acetamido-2-deoxy-β-D-glucopyranoside, 5-bromo-4-chloro-3-indolyl-2-acetamido-2-deoxy-β-D-glucopyranoside, 5-bromo-4-chloro-3-indolyl-2-acetamido-2-deoxy-β-D-galactopyranoside, and has a molar concentration in the medium of between 20 and 600 μM.

45. The medium of claim 44, wherein the chromogenic substrate is 5-bromo-4-chloro-3-indolyl-2-acetamido-2-deoxy-β-D-glucopyranoside, and has a molar concentration in the medium of 200 μM.

46. The medium of claim 19, wherein the nutrient base comprises a peptone in an amount of between 0.01 and 40 g per liter of medium, a yeast extract in an amount of between 0.01 and 40 g per liter of medium and a carbon source selected from glucose, glycerol, acetates, pyruvates, lactates, arginine and aminobutyrates, the amount of said carbon source ranging from 0 to 10 g per liter of medium.

47. The medium of claim 19, further comprising a buffer for adjusting the medium to a pH of between 5 to 8.5.

48. The medium of claim 19, further comprising agar in a proportion from 11 to 20 g/l, for example 15 g/l.

49. A kit for detecting yeasts of the species *Candida albicans* comprising (1) the medium of claim 19, and (2) a test chamber designed to allow both inoculation of a test sample into the medium and incubation of the test sample.

* * * * *